United States Patent [19]

Moncrief

[11] Patent Number: 4,575,870
[45] Date of Patent: Mar. 11, 1986

[54] REMOTE CONTROL OF INDUSTRIAL FLUOROSCOPE

[75] Inventor: William A. Moncrief, Detroit, Mich.

[73] Assignee: The United States of America as represented by the Secretary of the Army, Washington, D.C.

[21] Appl. No.: 166,722

[22] Filed: Jul. 7, 1980

[51] Int. Cl.[4] ............................................. G01N 23/04
[52] U.S. Cl. ....................................... 378/51; 378/99; 378/163; 378/196
[58] Field of Search ................ 250/360, 416 TV, 312; 358/100, 106, 111; 378/196, 51, 163, 190, 56, 99

[56] References Cited

U.S. PATENT DOCUMENTS 2,861,699 11/1958 Youmans ............................. 358/100
4,246,607 1/1981 Vijverberg ................... 250/416 TV

FOREIGN PATENT DOCUMENTS 7802858 9/1979 Netherlands ................. 250/416 TV
1210720 10/1970 United Kingdom ................ 358/111
1280758 7/1972 United Kingdom ................ 358/111

OTHER PUBLICATIONS

Angilello, "Method for Aligning Circuits on Substrates", IBM Tech. Discl. Bull., vol. 22, No. 6, Nov. 1979, pp. 2510-2511.

Primary Examiner—Alfred E. Smith
Assistant Examiner—Carolyn E. Fields
Attorney, Agent, or Firm—Peter A. Taucher; John E. McRae; Robert P. Gibson

[57] ABSTRACT

An industrial fluoroscope having a television camera optically trained on the area between the X-ray tube and the fluoroscope to provide pictorial information on the tube-test object spacing and the tube-fluoroscope spacing. The pictorial information is displayed on a television receiver remote from the X-ray room, hence safely away from the harmful X-rays. The televised information assists the human technician to remotely manipulate the test object and fluoroscope equipment without having to physically enter the X-ray room. A video recorder may be associated with the television receiver to provide a permanent record of the test object positionment in relation to the X-ray picture.

1 Claim, 4 Drawing Figures

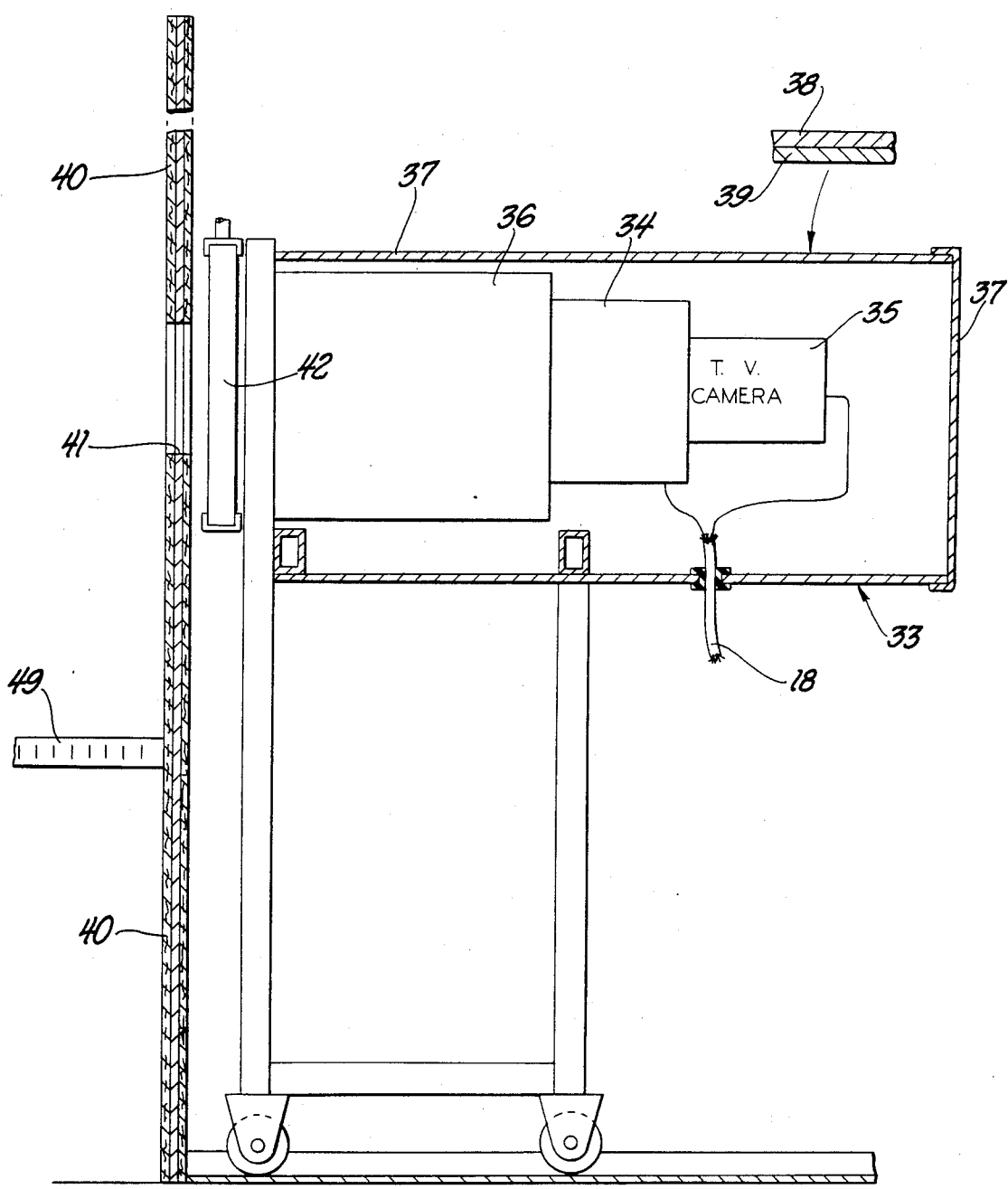
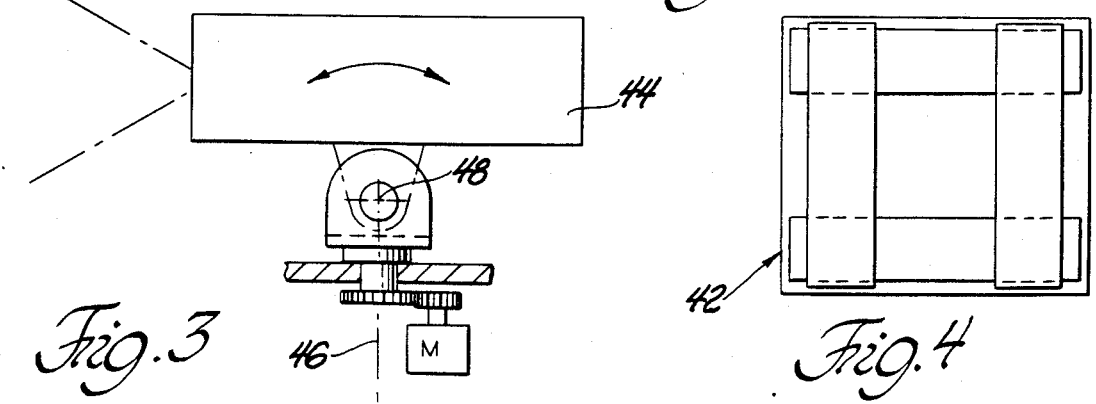

REMOTE CONTROL OF INDUSTRIAL FLUOROSCOPE

BACKGROUND AND SUMMARY OF THE INVENTION

In industrial fluoroscope nondestructive testing, the X-ray tube and fluoroscope are sometimes located in a room separate from the human technician; the walls of the room are of thick concrete or lead lined to protect him/her from harmful X-rays. This presents a problem in that the human technician is unable to see the test object; he/she has difficulty in remotely manipulating the test object or adjusting the fluoroscope equipment. The present invention proposes the addition of a television camera in the X-ray room to target on the area between the X-ray tube and fluoroscope, thereby providing desired information on the tube-test object spacing and the tubefluoroscope spacing without requirement for the technician to actually enter the room. The television camera is cableconnected to a television receiver at the technician station outside the X-ray room.

Television camera usefulness is augmented by the addition of a small mirror located near the X-ray tube to reflect into the camera an image of the external surface of the test object being irradiated by the X-ray beam. This provides the human technician with visual information on the external surface of the test object which he can correlate with test object internal structure information provided by the X-ray. The human technician therefore has greater assurance that the X-ray is beamed through the intended portion of the object. The aforementioned video recorder can be actuated to provide a permanent record of internal test object defects and corresponding external appearance of the test object optically aligned with the defect.

The invention described herein may be manufactured, used, and licensed by or for the Government for governmental purposes without payment to me of any royalty thereon.

THE DRAWINGS

FIG. 2 is an elevational view of a fluoroscope used in the FIG. 1 X-ray room.

FIG. 3 illustrates a television camera positioned in the FIG. 1 X-ray room.

Figure 1:
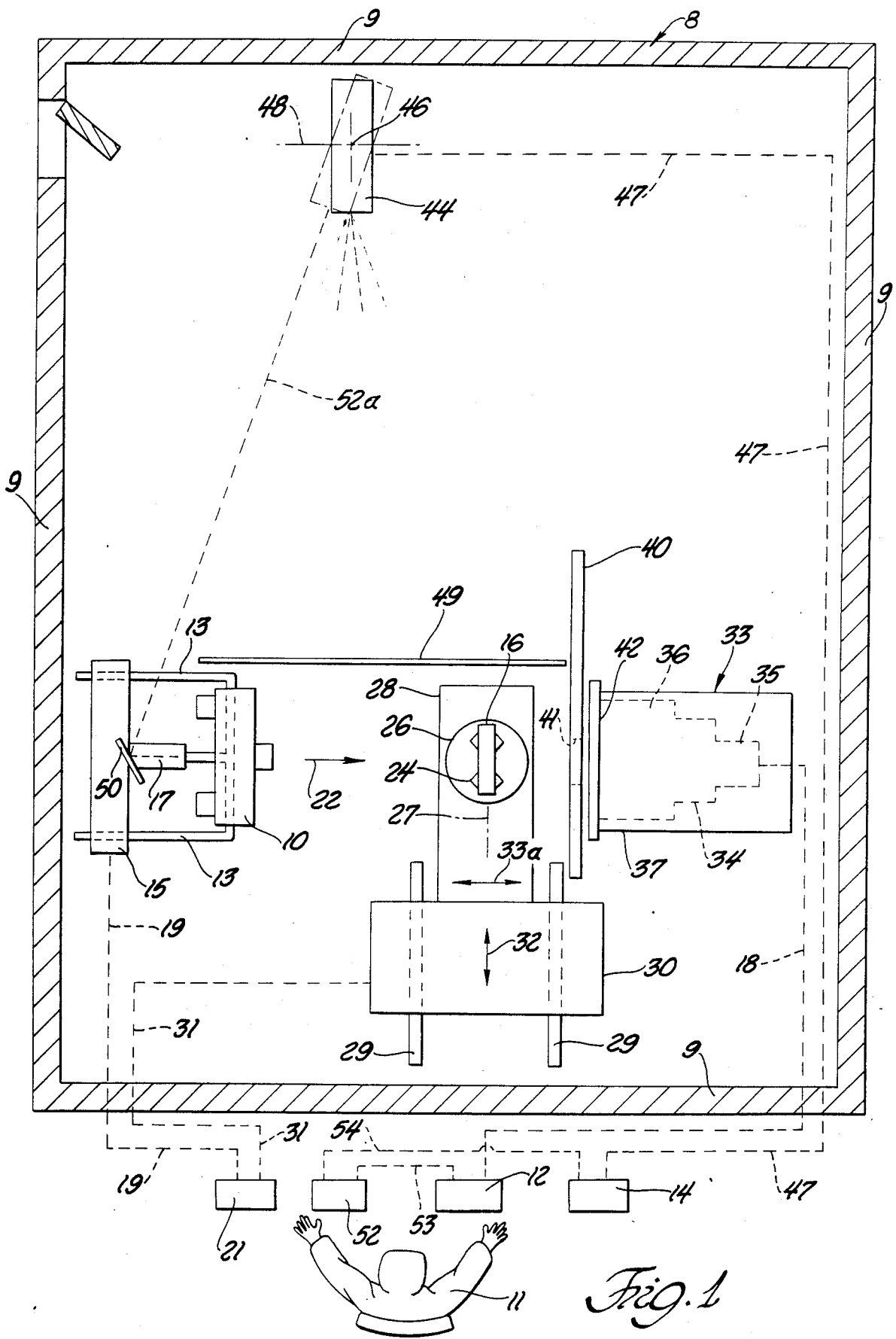
FIG. 1 is a plan view of an X-ray room incorporating the invention.

FIG. 4 schematically illustrates a shutter mechanism used on the FIG. 2 fluoroscope.

Referring in greater detail to the drawings, there is shown in FIG. 1 an X-ray room 8 defined by four walls 9, preferably of thick concrete or lead lined to confine harmful X-rays to the space within the room. A human technician 11 is stationed outside the room where he/she can operate certain controls and also view television receivers 12 and 14. Receiver 12 provides a picture of the internal structure of a test specimen or object 16, whereas receiver 14 provides a picture of the test object outer appearance.

Conventional X-ray tube 10 is positioned in the room to direct its output beam along sight line 22 through test object 16 positioned in a conventional chuck or jaw mechanism 24 carried by a powered turntable 26. Tube 10 is located on a carriage 13 that extends from an upstanding support 15 for adjusting movement along sight line 22; a hydraulic cylinder 17 is trained between support 15 and carriage 13 to provide the motive force for moving the carriage. Support 15 contains a second vertical hydraulic cylinder, not shown, for raising or lowering a section of the support; the mechanism acts like a conventional lift truck. The hydraulic cylinders are equipped with conventional control valves operated electrically through cables 19 that connect to a switch assembly 21 accessible to the human technician 11. Operation of selected switches in assembly 21 enables tube 10 to be adjusted vertically and also along sight line 22 for focusing on test object 16.

The aforementioned turntable 22 is rotatable around its vertical axis on a horizontal arm 28 that extends from a powered manipulator device 30 mounted for translational movement on floor tracks 29, as designated by arrow 32. A conventional system of motors and cables within manipulator 30 and arm 28 enables the arm to move vertically, laterally as designated by arrow 33a, or rotationally around arm axis 27, thereby providing five-way manipulative capability for test object 16 relative to X-ray beam direction line 22. Control cables 31 extend from the manipulator to control switch assembly 21 outside room 8.

X-rays passing through the test object impinge on a fluorescent screen within a fluoroscope assembly designated generally by numeral 33. The conventional fluoroscope preferably includes the fluoroscope 36 and an image intensifier 34 of the type generally described in U.S. Pat. No. 2,857,523 issued to L. Corso on Oct. 21, 1958. A conventional television camera 35 is trained on a fluorescent screen in the image intensifier to provide an electrical output representing the internal structure of the X-rayed object 16. Cables 18 transmit the camera output signal to the aforementioned television receiver 12.

As best shown in FIG. 2, the fluoroscope assembly includes motor-operated lead shutters 42 positioned at the ray entry end of a cabinet 37 that completely surrounds fluoroscope 36, image intensifier 34 and television camera 35. FIG. 4 shows the shutter assembly 42 as comprising a set of two vertically-extending rectangular slats and a set of two horizontally-extending rectangular slats. The cabinet 37 walls are formed to include an outer aluminum layer 38 and an inner layer or lining 39 of lead for shielding the cabinet interior space from X-rays generated by tube 10. Lead lining 39 is augmented by an upstanding barrier wall 40 positioned between the X-ray source 10 and cabinet 37. Conveniently wall 40 can include a massive lead plate, about one quarter inch thick, sandwiched between two facing sheets of plywood; a circular hole about nine inches in diameter permits passage of X-rays to fluoroscope 36. The shielding action of barrier wall 40 and cabinet 37 prevents external backscatter radiation from blurring the fluoroscope picture or otherwise adversely affecting the electrical output of camera 21.

The present invention is directed primarily to the addition of a second television camera 44 in the X-ray room to provide the human technician with information on the relative positions of test object 16, X-ray tube 10 and fluoroscope 36, as necessary for optimum detection of internal defects in the test object. FIG. 3 illustrates mechanism for adjusting the camera around vertical axis 46 and transverse axis 48. Torque motors energized by current supplied through cables 47 (FIG. 1) power the camera between its various positions. The camera has two principal positions, shown in FIG. 1 by full lines and dashed lines. In the full line position, the camera field-of-view covers the space between fluoroscope 36 and X-ray tube 10, thereby illustrating the spacing of test object 16 relative to tube 10 and fluoroscope 36. A stationary scale 49 in the camera field-of-view indicates the position of the fluoroscope and test object relative to X-ray tube 10. One set of wires in cable 47 connects camera 44 to television receiver 14, thereby providing the human technician with positional information on X-ray tube 10, the test object and fluoroscope 36.

In its dashed line position, camera 44 can be trained on a mirror 50 that is positioned on support 15 to reflect an image of test object 16 into the camera along optical line 52a. Preferably the television camera has a zoom-in and zoom-out lens construction that enables the camera to have a narrowed field-of-view along sight line 52a.

Television camera 44 enables the technician to adjust manipulator 30 and X-ray tube 10 for accurately orienting test object 16 relative to X-ray beam line 22, fluoroscope 36, and X-ray tube 10. Cameras 44 and 35 simultaneously transmit signals to receivers 12 and 14, which pictorially display the external and internal characteristics of the test object 16. With camera 44 targeted onto mirror 50, the human technician is enabled to pinpoint the location of an internal defect relative to the object external surface. To augment the utility of the system, I provide a video recorder 52 having cable connections 53 and 54 with the television receivers 12 and 14. Switches associated with cables 53 and 54 enable video recorder 52 to selectively make a permanent record of the internal defect appearing on the screen of receiver 12 and also the corresponding external surface of the test object shown on the screen of receiver 14. Recorder 52 enables the test procedures to be more readily duplicated or standardized, as necessary when similar test objects are to be tested at different times and by different human operators. After positionment of the test object in the jaw of chuck 24 the entire test operation can be controlled and recorded from outside the X-ray room.

I wish it to be understood that I do not desire to be limited to the exact details of construction shown and described for obvious modifications will occur to a person skilled in the art.

I claim:

1. In a nondestructive testing system comprising an x-ray room containing an x-ray tube (10) having an output beam axis (22); means (17) for moving the x-ray tube parallel to the output beam axis; a fluoroscope assembly (33) oriented to receive the x-ray beam, said fluoroscope assembly including a fluorescent screen; an object manipulator for supporting a test object in a variety of positions in the space between the fluoroscope screen and x-ray tube, said manipulator including an object-support arm structure (28) movable in a direction parallel to the aforementioned output beam axis to vary the spacing of the object from the x-ray tube and fluoroscope screen; a first television camera (35) optically trained on the aforementioned fluorescent screen to provide an electrical output representing the internal structure of the x-rayed object, a first television receiver (12) outside the x-ray room, and cable connections between the first television receiver and the first camera:

the improvement comprising a second television camera (44) having a first position in which it is optically trained on the area between the x-ray tube and the fluoroscope assembly with its field of view encompassing the tube-object spacing and the tube-fluoroscope spacing; a scale (49) extending parallel to the aforementioned output beam axis in the space between x-ray tube and fluoroscope assembly to give the second camera a measuring reference for the test object position; a mirror (50) located in close adjacency to the x-ray tube; said second television camera being swingable to a second position in which it is optically trained on the mirror; the mirror being oriented to reflect into the second camera the external surface of the object being irradiated by the x-ray beam; a second television receiver (14) outside the x-ray room; cable connections between the second television camera and second television receiver; and a video recorder (52) cableconnected to the first and second television receivers to provide a permanent record of the visual information on each receiver.

* * * * *